United States Patent [19]
Tassignon

[11] Patent Number: 6,027,531
[45] Date of Patent: Feb. 22, 2000

[54] INTRAOCULAR LENS AND METHOD FOR PREVENTING SECONDARY OPACIFICATION

[76] Inventor: Marie-José B. R. Tassignon, Wapenhaghestraat 10 IN 2600, Berchem-Antwerp, Belgium

[21] Appl. No.: 08/950,290

[22] Filed: Oct. 14, 1997

[51] Int. Cl.[7] ........................................................ A61F 2/16
[52] U.S. Cl. .................................. 623/6; 623/4; 128/898
[58] Field of Search .............................. 623/6, 4; 128/898

[56] References Cited

U.S. PATENT DOCUMENTS

| | | |
|---|---|---|
| 4,485,499 | 12/1984 | Castleman . |
| 4,547,915 | 10/1985 | Castleman . |
| 4,808,181 | 2/1989 | Kelman . |
| 5,002,571 | 3/1991 | O'Donnell, Jr. et al. . |
| 5,366,501 | 11/1994 | Langerman . |
| 5,370,687 | 12/1994 | Poler . |
| 5,405,385 | 4/1995 | Heimke et al. . |
| 5,445,636 | 8/1995 | Bretton . |
| 5,549,670 | 8/1996 | Young et al. . |
| 5,576,345 | 11/1996 | Mangnasson . |
| 5,593,438 | 1/1997 | Akhavi et al. . |
| 5,697,973 | 12/1997 | Peyman et al. ............................ 623/6 |

*Primary Examiner*—David H. Willse
*Assistant Examiner*—Dinh X. Nguyen
*Attorney, Agent, or Firm*—Darby & Darby

[57] ABSTRACT

An intraocular lens for use in extracapsular cataract extraction has a haptic pat that surrounds the optical pat of the lens and further contains a groove of such shape to accommodate the anterior and posterior capsules of the lens bag after anterior capsulorhexis, extracapsular cataract extraction and posterior capsulorhexis. The lens is preferably inserted in a calibrated, circular and continuous combined anterior and posterior capsulorhexis, slightly smaller than the inner circumference of the groove as to induce a stretching of the rims of the capsular openings. This new approach is believed to prevent the appearance of secondary opacification of the capsules, allows a very stable fixation of the intraocular lens and ensures a tight separation between the anterior and posterior segment of the eye. This new principle of insertion is called the bag-in-the-lens technique, in contrast with the classical lens in-the-bag technique.

8 Claims, 2 Drawing Sheets

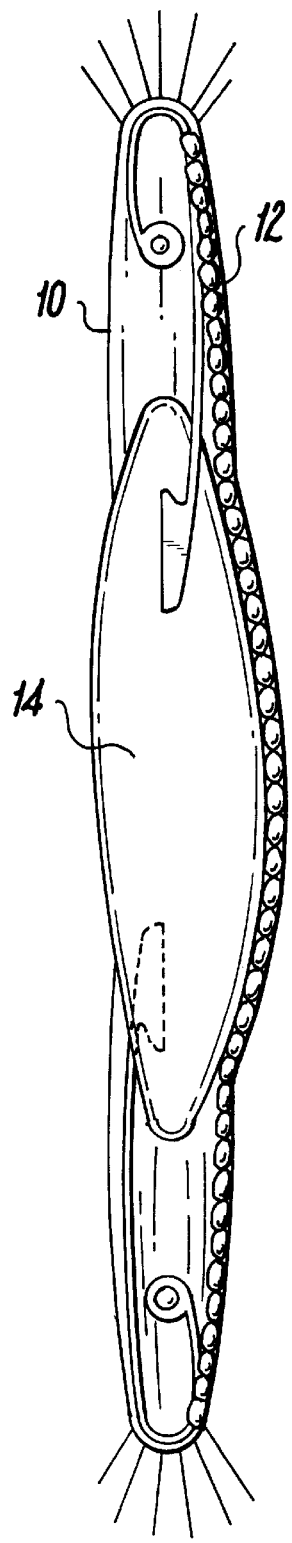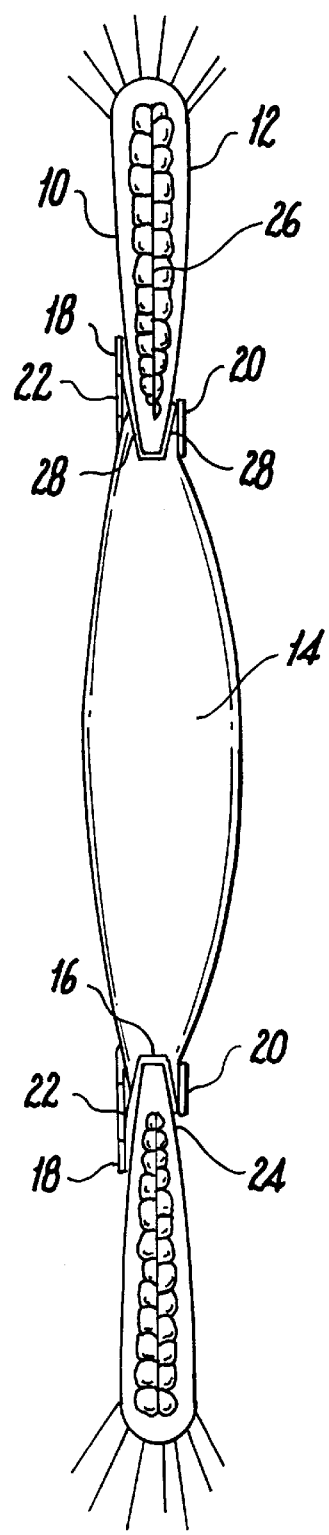
Fig. 1A
PRIOR ART
Fig. 1B

INTRAOCULAR LENS AND METHOD FOR PREVENTING SECONDARY OPACIFICATION

BACKGROUND OF THE INVENTION

1. Field of the Invention

This invention relates generally to the field of intraocular lenses after cataract extraction and in particular to intraocular lenses that reduce secondary opacification of the lens capsules.

2. Description of Prior Art

The insertion of an artificial intraocular lens in the human eye is a well-known surgical procedure to cure cataract, a common eye disorder in which the natural lens becomes gradually less transparent.

Typically in such a procedure, the opaque lens material is removed from the lens bag, and is replaced by an artificial intraocular lens with the same optical properties. Several lens types have been designed since the original idea of Ridley in 1949. These types include e.g. anterior chamber angle supported lenses, iris supported lenses, posterior chamber sulcus fixated lenses, and in-the-bag lenses. None of these lenses have the property of preventing the secondary opacification of the posterior capsule of the lens bag. This secondary opacification is due to a proliferation of the remaining epithelial cells in the lens bag. Ultimately, after a variable time interval, secondary opacification occurs in up to eighty percent of the operated eyes. Many remedies, largely unsuccessful, have been advocated to prevent this major cause of visual loss after cataract surgery. These include the introduction of chemical substances with the intraocular lens [salts, U.S. Pat. No. 5,370,687 to Poler; taxol, U.S. Pat. No. 5,576,345 to Mangnasson], the physical removal of remaining proliferative cells within the lens bag [use of probe, U.S. Pat. No. 5,445,636 to Bretton], and special lens designs that include metal coatings [U.S. Pat. No. 5,593,438 to Akhavi], adhesive coatings [U.S. Pat. No. 5,002,571 to O'Donnell], roughened surfaces on the lens [U.S. Pat. Nos. 5,405,385 to Heimke, 4,808,181 to Kelman, 5,549,670 to Young], or mechanical with multiple fixation rings attached to the intraocular lens [U.S. Pat. No. 5,366,501 to Langerman]. The only efficient cure for an established secondary opacification of the posterior capsule at present is the surgically induced rupture of the opaque posterior capsule, or capsulotomy, with a capsulotomy needle or with a Nd-YAG Q switched laser. A specially designed intraocular lens can be helpful in aforementioned surgical procedures [U.S. Pat. No. 4,485,499 and 4,547,915 to Castleman]. These secondary capsulotomies however increase the complication rate after cataract surgery to the level of the older, now mostly abandoned intracapsular technique of cataract extraction. Complications e.g. include retinal detachment, glaucoma, cystoid macular edema and pitting of the intraocular lens.

All the intraocular lenses mentioned in prior art have a common feature. They are all placed in the lens bag and they do not prevent the proliferation of the remaining capsular epithelial cells behind the optical pat of the intraocular lens with opacification as a result. Even the surgical removal of the central pat of the posterior capsule immediately before implantation does not prevent further cellular proliferation. I have demonstrated recently that these cells do not need the support of the capsule to further proliferate and to reclose the opening of the posterior curvilinear continuous capsulorhexis (PCCC).

OBJECTS AND ADVANTAGES OF THE INVENTION

The principal object of this invention is therefore the design of an intraocular lens implant that is believed to prevent the secondary opacification of the posterior capsule. This goal will be achieved by taking four principles into account.

A. The intraocular lens has grossly the shape of a biconvex lens with a central, round optical part and a circular equatorial groove in the surrounding haptic part.

B. This lens is placed in, and supported by both the anterior and posterior lens capsules of the bag. The capsules have been previously opened by the method of a curvilinear continuous capsulorhexis. The lens bag is placed in the groove of the intraocular lens, hence the term bag-in-the-lens technqiue.

C. The calibration of the anterior and posterior capsular opening is important since the opening will have to be slightly smaller than the circumference of the inner diameter of the lens groove in order to stretch the capsular openings when inserting the lens. This stretching of the rims of the capsular openings will block the proliferation of the cells that will be captured in a closed space or environment, provided by the circular equatorial groove. We now know experimentally that cell proliferation is inhibited in a closed space. Additionally, this stretching will induce a further coalescence of anterior and posterior capsular layers and cause circular traction folds in which the proliferating cells are captured.

D. It is also known experimentally that a circular opening in the lens capsules will always shrink, and not dilate, due to a proliferation of remaining modified epithelial cells in the lens bag. These cells assume smooth muscle cell characteristics. The resultant shrinkage of the capsule openings will improve the stability of the lens fixation, and prevent a possible luxation of the intraocular lens, out of the capsular openings into the vitreous or anterior chamber.

Also, in my lens design, the haptic part of the lens is minimal and the optical part is maximal, resulting in a reduced weight, important for an increased stability. Another and major advantage of the shrinkage will be a perfect and tighter junction between the lens and the capsules, and thus a perfect separation between anterior and posterior segments of the eye; that result cannot be obtained by any other implant lens.

DESCRIPTION OF THE DRAWINGS

Features and advantages of the invention will appear from the following description of preferred embodiments of the invention, taken together with the drawings in which:

FIG. 1A is an anatomical cut through the anterior segment of the eye, illustrating the positioning of a conventional in-the-bag intraocular lens after removal of an anterior curvilinear continuous capsule portion of the lens bag, as well as the lens material between the remaining capsules of the lens bag. The occurrence of capsular opacification is schematically illustrated by the presence of cells lining the posterior capsular surface, the so called Elschnig pearls.

FIG. 1B is an anatomical cut through the anterior segment of the eye, showing the positioning of the new intraocular lens with the merged anterior and posterior capsules of the lens bag captured in the groove, a bag-in-the-lens configuration. Note the circular folds secondary to the stretching, and the tight junction at the level of the groove.

Figure 2A:
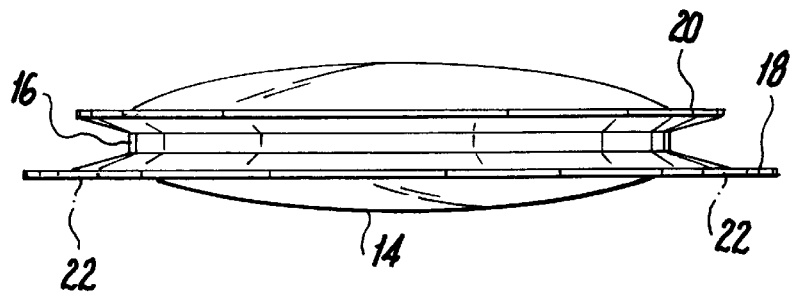
FIG. 2A is a side view of the intraocular lens, showing the characteristic groove in which the merged anterior and posterior lens capsules of the lens bag will settle.

REFERENCE NUMERALS IN DRAWINGS
10. Anterior capsule of the lens bag
12. Posterior capsule of the lens bag
14. Central and circular optical part of the intraocular lens
16. Groove in the haptic part of the intraocular lens
18. Anterior lip of the haptic part
20. Posterior lip of the haptic part
22. Perforation within an extension of the anterior lip
24. Folds in the merged anterior and posterior capsule of the lens bag
26. Closed space or environment containing the proliferating lens epithelial cells.
28. Tight junction between the intraocular lens and capsules.

DESCRIPTION OF PREFERRED EMBODIMENTS

Figure 2B:
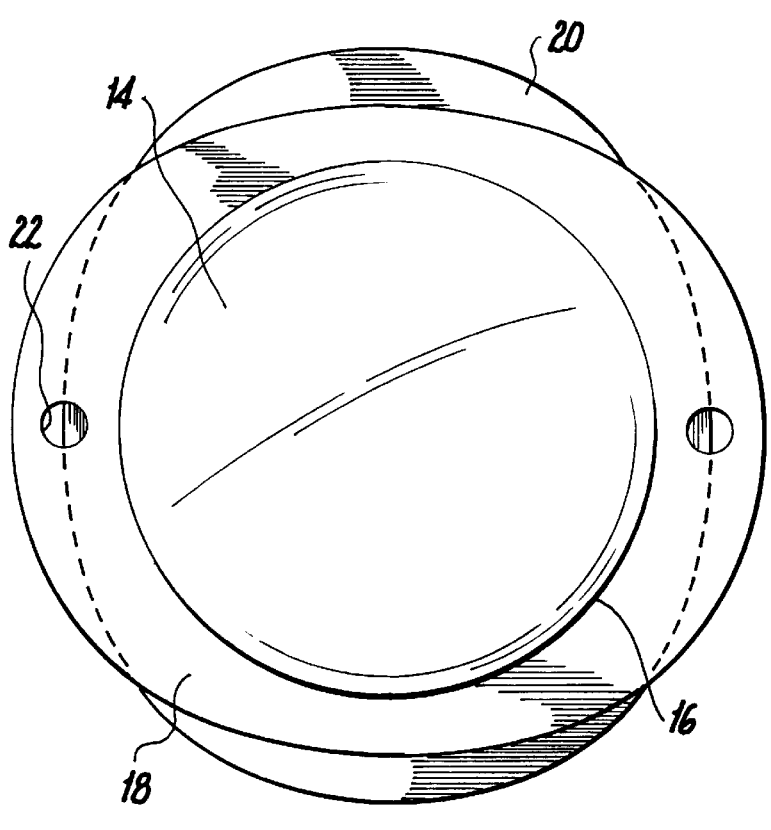
FIG. 2B is a view from above of the intraocular lens, illustrating the main central and circular optical part surrounded by the haptic part, consisting of a circumference that contains a groove. Both lips of the groove can have extended portions to facilitate the positioning and fixation of the capsules in the groove. The lips of the groove can have perforations to facilitate the manipulation of the lens.
Figure 2C:
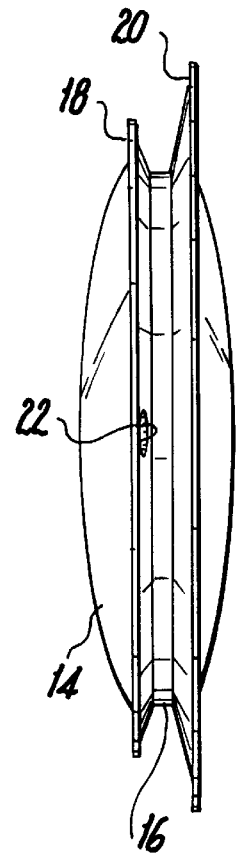
FIG. 2C is another side view of the intraocular lens illustrating the groove and perpendicularly oriented extensions of both lips of the groove.

FIGS. 1A and 1B illustrate the difference in concept of the lens in-the-bag fixation technique, FIG. 1A, as currently used by ocular surgeons, and the novel bag-in-the-lens fixation technique, FIG. 1B. In order to realize this new principle of lens fixation, the lens design has been changed as shown in FIGS. 2A, 2B and 2C. The preferred embodiment of the optical pat 14 of the intraocular lens is circular and biconvex although other configurations and shapes may be employed. The optical part 14 of the intraocular lens may be constructed of any of the currently used materials for rigid optics such as polymethylmetacrylate (PMMA), or deformable optics such as silicone polymeric materials, acrylic polymeric materials, hydrogel forming polymeric materials and mixtures of these materials or the like. The lens materials used can be coated with chemicals for various purposes, as illustrated in the prior art. The diameter of the optical part 14 of the intraocular lens can be variable but should not be less than 5 mm for reasons of optical quality and for ease of centration. The optical part 14 can be designed for monofocal or multifocal purposes.

The circumferential haptic part of the intraocular lens consists of an anterior lip 18 and posterior lip 20, defining a groove 16 in between. The haptic part of the intraocular lens is preferably made of one piece with the optical part 14 of the intraocular lens. It can however be affixed to the optical part 14 if this is more convenient for production purposes. The haptic part may be constructed from any of the commonly employed materials as previously described.

The posterior lip 20 of the haptic part of the intraocular lens can have extensions to create an oval shape. This shape facilitates insertion of the posterior lip 20 behind the opening of the anterior and posterior capsulorhexis, as explained in the surgical procedure. This oval shape is purely illustrative and may be of other configuration as long as a good insertion and fixation of the intraocular lens can be provided. E.g. prong-like, open loop or closed loop extensions are possible.

The anterior lip 18 of the haptic part of the intraocular lens has also an oval shape, perpendicularly oriented with regard to the oval shape of the posterior lip 20. The suggested shape and orientation of the anterior lip 18 helps in preventing the inadvertent luxation of the intraocular lens in the space of Berger during or after surgery. Different configurations are possible, as mentioned before.

The length of both anterior 18 and posterior 20 lips will thus typically vary between 1 and 2 mm, but can be longer, especially in the absence of a good calibration of the size of anterior and posterior capsulorhexis. Perforations 22 can be added to the anterior 18 or posterior lip 20 of the haptic part, allowing easier manipulation of the intraocular lens. These perforations 22 can be of variable number and size.

The groove 16 in the haptic part of the intraocular lens is delineated by the anterior 18 and posterior 20 lips of the haptic part, and the optical part 14 of the intraocular lens. It can be of variable width, depth and shape in order to capture the merged anterior and posterior capsules, obtained after curvilinear continuous capsulorhexis. Various inner or smaller diameters of the groove 16 are provided to correspond to various sizes of capsulorhexis. A typical groove 16 will taper from 0.5 mm to 0.2 mm in width at its inner or smallest diameter.

DESCRIPTION OF A PREFERRED SURGICAL PROCEDURE

The surgical procedure consists of a number of steps which are currently used in conventional extracapsular cataract extraction, some of which have to be modified, and in a number of new steps that are necessary to insert the new intraocular lens in the most optimal fashion.

The opening of the anterior chamber and the filling of the anterior chamber with viscoelastics are well known steps in the prior art. The anterior curvilinear continuous capsulorhexis must be modified in such way that the diameter of this rhexis is slightly smaller than the smaller diameter of the lens groove 16. I.e. the anterior rhexis must be calibrated. Typically, the diameter of the rhexis would be 1 to 1,5 mm smaller. The anterior capsulorhexis must be well centered on the visual axis of the eye. After the anterior capsulorhexis is performed, the lens consisting of nucleus and cortical material, is removed in the usual manner for an extracapsular cataract extraction technique. The posterior curvilinear continuous capsulorhexis must then be executed in such way that its diameter is the same as the diameter of the anterior capsulorhexis. The openings of both anterior and posterior capsulorhexis should match each other as close as possible in size, location and centration. The technique of making the posterior rhexis is the same as the one that is currently used in conventional extracapsular cataract extraction. A puncture is made in the center of the posterior capsule. The posterior capsule is then separated from the anterior hyaloid of the vitreous by injection of viscoelastic material through the puncture in the space of Berger. After this step a calibrated posterior curvilinear continuous capsulorhexis can be performed in the usual manner.

The insertion of the intraocular lens using the bag-in-the-lens technique is new. It is different from the conventional lens-in-the-bag insertion technique. First, the lens is introduced into the anterior chamber of the eye. Then the posterior lip 20 of the haptic part of the intraocular lens is placed behind the rim of the opening of the posterior capsule in the space of Berger and the anterior lip 18 of the haptic part of the intraocular lens is placed before the rim of the opening of the anterior capsulorhexis.

Because the diameters of both the anterior and posterior capsulorhexis are identical but slightly smaller than the smaller diameter of the lens groove 16, the capsular openings will be stretched when inserting the lens, thus providing a tight junction 28 around the intraocular lens and a closed space 26 or environment that contains the remaining proliferating epithelial cells of the lens bag. Contraction of the remaining and captured cells with smooth muscle characteristics, will provide circular tractional folds 24 in the merged anterior and posterior capsules of the lens bag. This contraction further improves the tight junction 28 between the capsules and intraocular lens.

SUMMARY, RAMIFICATIONS, AND SCOPE

The new intraocular lens is specifically designed for insertion of the remainder of the lens bag, consisting of the merged anterior and posterior capsules obtained after calibrated curvilinear continuous capsulorhexis, in a circumferential groove of the lens. Some significant advantages include the prevention of secondary opacification of the lens bag, increased stability of fixation inside the merged lens capsules and a tight junction between the lens and capsules, providing a good separation between the anterior and posterior ocular compartments.

The intraocular lens can be made of various biocompatible materials, rigid or foldable. The haptic part and groove can be of different shape and can have several prong-like extensions. Some of these extensions can be perforated for both fixation or rotation purposes. The optical part can be of different diameters.

Although the above description contains many specifications, these should not be construed as limiting the scope of the invention but as merely providing illustrations of some of the presently preferred embodiments of this invention. Other embodiments of the invention, including additions, subtractions, deletions, or modifications of the disclosed embodiment will be obvious to those skilled in the art and are within the scope of the following claims. As such, the scope of the invention should be determined by the appended claims and their legal equivalents.

What is claimed is:

1. An intraocular lens for receiving the lens bag of an eye in which the natural lens has been removed and matching circular openings in the anterior and posterior capsule of said lens bag have been created, said intraocular lens comprising:

a central optical part for projecting an image on the retina of said eye;

a peripheral haptic part surrounding said central optical part, said peripheral haptic part having an inner diameter that is slightly larger than said matching circular openings in the anterior and posterior capsule of the lens bag over the entire 360° circumference, said peripheral haptic part having an outer diameter that is sufficiently large enough to provide a stable fixation of said intraocular lens in said eye, and the maximum axial thickness of said peripheral haptic part is less than or equal to the minimum axial thickness of said central optical part;

wherein, said peripheral haptic part further comprising an anterior lip and a posterior lip, said anterior and posterior lip delineating a circumferential groove of such width and depth to accommodate said matching circular openings in the anterior and posterior capsule of the lens bag; and whereby, the implantation of said intraocular lens minimizes the risk of secondary opacification of said lens bag and the risk of luxation inside said eye.

2. An intraocular lens according to claim 1, wherein said interior lip and said posterior lip have an oval shape, thereby facilitating the insertion of said lens bag in said lens.

3. An intraocular lens according to claim 1, wherein the oval shape of said anterior lip is disposed perpendicularly with respect to the oval shape of said posterior lip.

4. An intraocular lens according to claim 1, wherein said intraocular lens is made from deformable materials, whereby said intraocular lens is foldable before insertion into said eye.

5. A method for inserting the lens bag of an eye into an intraocular lens comprising of an optic part and a haptic part, said haptic part having a maximum axial thickness that is less than or equal to the minimum axial thickness of said optic part, said haptic part further comprising an anterior lip, a posterior lip and a circumferential groove, and said method comprising the steps of:

opening said eye;

removing a circular part of the anterior capsule of said lens bag of said eye to create a first opening in said lens bag;

removing the natural lens of said eye;

removing a circular pat of the posterior capsule of said lens bag of said eye to create a second opening matching the first opening in said lens bag;

sizing the removed circular part of the anterior capsule and of the posterior capsule so that said circumferential groove in said haptic part encompasses an area slightly larger than an area encompassed by said first and second openings;

placing said lens bag in said circumferential groove of said intraocular lens, thereby minimizing the risk of secondary opacification and luxation; and closing said eye.

6. A method according to claim 5, said method further comprising the step of:

making said intraocular lens from deformable materials so that said intraocular lens can be folded before insertion into said eye.

7. A method according to claim 5, said method further comprising the step of:

forming said anterior lip and said posterior lip in an oval shape to facilitate insertion of said lens bag in said circumferential groove and to minimize the risk of luxation.

8. A method according to claim 7, wherein said forming step further comprises forming the oval shape of said anterior lip perpendicularly with respect to the oval shape of said posterior lip.

* * * * *

UNITED STATES PATENT AND TRADEMARK OFFICE
CERTIFICATE OF CORRECTION

PATENT NO. : 6,027,531
DATED : February 22, 2000
INVENTOR(S) : Marie-Jose B. R. TASSIGNON It is certified that errors appear in the above-identified patent and that said Letters Patent is hereby corrected as shown below:

On the title page:

Item [76] Inventor, Change "WAPENHAGHESTRAAT 10 IN 2600" to WAPENHAGHESTRAAT 6 IN 2600--.

Signed and Sealed this

Nineteenth Day of December, 2000

Attest:

Q. TODD DICKINSON

*Attesting Officer*  *Commissioner of Patents and Trademarks*